United States Patent [19]
Sax

[11] Patent Number: 5,978,698
[45] Date of Patent: Nov. 2, 1999

[54] ANGIOPLASTY PROCEDURE USING NONIONIC CONTRAST MEDIA

[75] Inventor: Frederic L. Sax, Villanova, Pa.

[73] Assignee: Merck & Co., Inc., Rahway, N.J.

[21] Appl. No.: 08/943,872

[22] Filed: Oct. 8, 1997

Related U.S. Application Data

[60] Provisional application No. 60/028,919, Oct. 8, 1996.

[51] Int. Cl.[6] .......................................... A61B 6/00
[52] U.S. Cl. ............................ 600/431; 424/9.1; 128/898
[58] Field of Search ........................... 128/898; 600/431; 424/9.1; 514/331, 401, 422, 79, 255, 318, 326

[56] References Cited

U.S. PATENT DOCUMENTS

| | | |
|---|---|---|
| 5,281,585 | 1/1994 | Duggan et al. . |
| 5,292,756 | 3/1994 | Duggan et al. . |

OTHER PUBLICATIONS

Grollman, Jr. et al., Cathetarization and Cardiovascular Diagnosis, "Thromboembolic Complications in Coronary . . . ", vol. 14, pp. 159–164 (1988).

Hwang et al., Cathetarization and Cardiovascular Diagnosis, "The Potential Risk of Thrombosis During Coronary . . . ", vol. 16, pp. 209–213 (1989).

Doorey et al., Clin. Cardiol., "Catastrophic Thrombus Development Despite Systemic Heparinization . . . ", vol. 15, pp. 117–120 (1992).

Gasperetti et al., J. Am. Coll. Cardiol., "Influence of Contrast Media on Thrombus Formation During Coronary Angioplasty", vol. 18(2), pp. 443–450 (1991).

Grines et al., J. Am. Coll. Cardiol., "A Randomized Trial of Low Osmolar Ionic Versus Nonionic Contrast Media in Patients with . . . ", vol. 27(6), pp. 1381–1386 (1996).

Landau et al., New England Journal of Medicine, "Medical Progress—Percutaneous Transluminal Coronary Angioplasty", vol. 330(14), pp. 981–993 (1994).

*Primary Examiner*—Mickey Yu
*Assistant Examiner*—Kelly O'Hara
*Attorney, Agent, or Firm*—Richard S. Parr; Melvin Winokur

[57] ABSTRACT

A method for treating patients in need of percutaneous transluminal coronary angioplasty which comprises administering nonionic contract media to the patient and treating the patient with a fibrinogen receptor antagonist.

7 Claims, No Drawings

ANGIOPLASTY PROCEDURE USING NONIONIC CONTRAST MEDIA

This application claims benefit of Provisional application Ser. No. 60/028,919, filed Oct. 8, 1996.

BACKGROUND OF THE INVENTION

Angioplasty procedures are commonly performed on patients having coronary blockages. An estimated 2 million coronary angiographic procedures are performed annually in the United States alone. The objective of angioplasty procedures is to revascularize the coronary artery where the blockage is located. By inflating a balloon at the point of blockage, blood flow is restored.

Contrast dye is used to initially identify the presence and location of the blockage. It is also used during the procedure to provide an image for proper placement of the guide wire, catheter, and angioplasty balloon.

There are key differences among radiographic contrast media. Ionic contrast media are far less expensive than nonionic contrast media. However, ionic contrast media are associated with several infrequent side effects of modest clinical significance including nausea, vomiting and allergic reactions. Bradycardia, abnormalities in repolarization manifest by ST segment and T wave alterations, depression of ventricular systolic function and lowering of systolic blood pressure occur commonly with ionic contrast media but last only seconds.

The side effects associated with ionic contrast media are rare with nonionic contrast agents. However, reports of thrombotic events occurring during routine angiography with nonionic media suggest that nonionic media may be a procoagulant (Grollman et al., Cathet. Cardiovasc. Diagn. (1988) vol. 14 pp. 159–64 and Hwang et al., Cathet. Cardiovasc. Diagn. (1989) vol. 16 pp. 209–13). Studies of percutaneous coronary interventions (which are inherently associated with a heightened risk of intracoronary thrombus formation) have reported increased thrombus formation with nonionic contrast agent use (Doorey ey al., Clin. Cardiol. (1992) vol. 15 pp. 117–20 and Gasperetti et al., J. Am. Coll. Cardiol. (1991) vol. 18 pp. 443–50). Grines et al., JACC (1996) vol. 27, no. 6 pp. 1381–6 conclude that in patients with unstable ischemic syndromes undergoing coronary angioplasty, the use of ionic low osmolality contrast media reduces the risk of ischemic complications acutely and at 1 month after the procedure. Grines et al. recommend that ionic media be strongly considered when performing interventions in patients with unstable angina or myocardial infarction.

It is known that acute or abrupt closure occurs in 2–8% of patients undergoing percutaneous transluminal coronary angioplasty and accounts for most of the short-term morbidity and mortality associated with the procedure. In about 75% of patients with abrupt closure, it occurs within minutes after percutaneous transluminal coronary angioplasty, when they are still in the catheterization laboratory. In the other 25%, it usually occurs within 24 hours after the procedure (Landau et al. New England Journal of Medicine vol. 330 No. 14 p. 986 (1994)).

Glycoprotein IIb/IIIa Fibrinogen Binding Inhibitors

Fibrinogen receptor antagonists, which inhibit the binding of fibrinogen to the glycoprotein IIb/IIIa ($\alpha$II$\beta$3) platelet receptor site, may be administered during and following angioplasty procedures to reduce the risk of ischemic events. Because the period of time following angioplasty procedures is associated with a higher level of coronary ischemic events, fibrinogen receptor antagonists are administered following angioplasty to inhibit fibrinogen binding to the glycoprotein IIb/IIIa platelet receptor site, reducing the level of ischemic events.

Integrelin is a cyclic peptide that is based on the KGD sequence in the snake venom protein barbourin. It inhibits ligand binding to glycoprotein IIb/IIIa. Among the non-peptide compounds are Ro 44–9883 and MK-383, which are administered intravenously, and are also selective for glycoprotein IIb/IIIa. Orally active agents include SC54684, which is a prodrug (i.e., it requires biotransformation in vivo to its active form) with high oral bioavailability and RO43–8857, GR144053, and DMP728, which are themselves the active inhibitors. Literally thousands of other compounds have been synthesized in an attempt to obtain optimal potency, metabolic stability, receptor specificity, and favorable intravascular survival. Despite variations in these compounds, virtually of all of them retain the basic charge relations of the RGD sequence with a positive charge separated from a negative charge by approximately 10–20 Å. All of these compounds inhibit fibrinogen binding to the glycoprotein IIb/IIIa platelet receptor site. Monoclonal antibody 7E3 also blocks the glycoprotein IIb/IIIa receptor.

We have now found that angioplasty procedures conducted with nonionic contrast media, in combination with glycoprotein IIb/IIIa receptor antagonist administration, reduce the risk of ischemic complications (follow-up intervention associated with acute coronary ischemic syndrome, e.g. coronary artery bypass grafting, repeat percutaneous intervention for acute ischemia, insertion of a coronary endovascular stent) to a greater degree than procedures involving ionic contrast media with glycoprotein IIb/IIIa receptor antagonists, procedures involving nonionic contract media without glycoprotein IIb/IIIa receptor antagonists, or procedures involving ionic contrast media without glycoprotein IIb/IIIa receptor antagonists.

SUMMARY OF THE INVENTION

The invention is a method for diagnosing and treating a patient having coronary artery blockage which comprises a) introducing nonionic contrast dye into the coronary artery of the patient to image the blockage, and b) imaging the blockage with a nonionic contrast dye, administering a fibrinogen receptor antagonist to the patient, and inflating a balloon at the location of the coronary blockage to revascularize the artery, and c) administering fibrinogen receptor antagonist to the patient following balloon inflation.

The fibrinogen receptor antagonist is administered to the patient during balloon inflation, and for a period of time of at least 24 hours subsequent to balloon inflation. The fibrinogen receptor antagonist may be orally or intravenously administered.

When intravenously administered, the fibrinogen receptor antagonist can be, for example, Mpr-(Acetimidyl-Lys)-Gly-Asp-Trp-Phe-Cys-NH$_2$, Mpr-(Acetimidyl-Lys)-Gly-Asp-Trp-Phe-Pen-NH$_2$, Mpr-(Phenylimidyl-Lys)-Gly-Asp-Trp-Phe-Pen-NH$_2$, Mpr-(Phenylimidyl-Lys)-Gly-Asp-Trp-Phe-Cys-NH$_2$, N-Methyl-D-phenylalanyl-N-[(1S)-1-fonnyl-4-guanidinobutyl]-L-prolinamide, ((1-(2-((4-(aminoiminomethyl)benzoyl)amino)-3-(4-hydroxyphenyl)-1-oxopropyl)-4-piperidinyl)oxy)-(S)-acetic acid, N-(2-(2-(((3-((aminoiminomethyl)amino)propyl)amino)carbonyl)-1-piperidnyl)-1-(cyclohexylmethyl)-2-oxoethyl)-(R,S)-glycine, and (2-S-(n-Butylsulfonylamino)-3[4-(piperidin-4-yl) butyloxyphenyl]propionic acid hydrochloride, When orally administered, the fibrinogen receptor antagonist can be, for example, 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4] diazepin-2-yl]carbonyl]-amino]propionic acid, Methyl-N$^3$-[2-{3-(4-formamidinophenyl)-isoxazolin-5(R)-yl}-acetyl]-N$^2$-(n-butyloxycarbonyl)-2,3-(S)-diaminopropionate acetate salt, Ethyl 3-[[4-[[4-(aminoiminomethyl)phenyl]amino]-1,4-dioxobutyl]amino]-4-pentynoate, or.

(R)-methyl-3-[[[3-[4-(aminoiminomethyl)phenyl]-4,5-dihydro-5-isoxazolyl]acetyl]amino]-N-(butoxycarbonyl)-L-alanine monoacetate.

The invention is a method for treating patients having coronary blockage in an artery which comprises imaging the blockage with a nonionic contrast dye, administering a fibrinogen receptor antagonist to the patient, and inflating a balloon at the location of the coronary blockage to revascularize the artery.

DETAILED DESCRIPTION OF THE INVENTION

The method encompasses a treatment for patients having coronary blockages involving the use, in a manner ordinary to angioplasty procedures, of nonionic contrast media, in conjunction with administration, during the treatment, of a fibrinogen receptor antagonist. The objective of the treatment is to remove coronary blockages. The treatment results in lower incidence of ischemic events when compared with procedures using nonionic dye without fibrinogen receptor antagonist, ionic dye with fibrinogen receptor antagonist, or ionic dye without fibrinogen receptor antagonist.

Antagonists for the glycoprotein IIb/IIIa fibrinogen receptor have been described in U.S. Pat. Nos. 5,470,849, 5,463,011, 5,455,243, 5,451,578, 5,446,056, 5,441,952, 5,422,249, 5,416,099, 5,405,854, 5,397,791, 5,393,760, 5,389,631, 5,380,713, 5,374,622, 5,358,956, 5,344,783, 5,340,798, 5,338,7235,334,596, 5,321,034, 5,318,899 (e.g. cyclic heptapeptides Mpr-(Acetimidyl-Lys)-Gly-Asp-Trp-Phe-Cys-NH$_2$, Mpr-(Acetimidyl-Lys)-Gly-Asp-Trp-Phe-Pen-NH$_2$, Mpr-(Phenylimidyl-Lys)-Gly-Asp-Trp-Phe-Pen-NH$_2$, and Mpr-(Phenylimidyl-Lys)-Gly-Asp-Trp-Phe-Cys-NH$_2$, wherein Mpr is mercapto propionyl),5,312,923, 5,294,616, 5,292,756, 5,281,585 5,272,158, 5,264,420, 5,260,307, 5,239,113 (e.g. Ethyl 3-[[4-[[4-(aminoiminomethyl)phenyl] amino]-1,4-dioxobutyl]amino]- 4-pentynoate), 5,227,490, 5,206,373, 4,703,036 (e.g. N-Methyl-D-phenylalanyl-N-[(1S)-1-fomyl-4-guanidinobutyl]-L-prolinamide), EP 505 868 (e.g. ((1-(2-((4-(aminoiminomethyl)benzoyl)amino)-3-(4-hydroxyphenyl)-1-oxopropyl)-4-piperidinyl)oxy)-(S)-acetic acid) WO 9311152 (e.g. N-(2-(2-(((3-((aminoiminomethyl)amino)propyl)amino)-carbonyl)-1-piperidnyl)-1-(cyclohexylmethyl)-2-oxoethyl)-(R,S)-glycine), EP 333 356, WO 9514683 (e.g. (Methyl-N$^3$-[2-{3-(4-formamidinophenyl) -isoxazolin-5 (R)-yl }-acetyl]-N$^2$-(n-butyloxycarbonyl)-2,3-(S)-diaminopropionate acetate salt), (R)-methyl-3-[[[3-[4-(aminoiminomethyl)phenyl]-4,5-dihydro-5-isoxazolyl]acetyl]amino]-N-(butoxycarbonyl)-L-alanine monoacetate, and WO 9422820. They are described as useful for inhibiting fibrinogen binding and inhibiting clot formation.

Glycoprotein IIb/IIIa receptor antagonists and their pharmaceutically acceptable salts are useful in the present invention. The term "pharmaceutically acceptable salts" means non-toxic salts of the compounds which include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexykesorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Pharmaceutically effective amounts of the glycoprotein IIb/IIIa receptor antagonists are suitable for use in the compositions and methods of the present invention. The term "pharmaceutically effective amount" means that amount of a drug or.pharmaceutical agent that will elicit the biological or medical response of a tissue, system or animal that is being sought by a researcher or clinician.

The methods of the present invention are useful in combination with procedures for treating patients with other anticoagulants (e.g. heparin and warfarin), thrombolytic agents (e.g. streptokinase and tissue plasminogen activator), and platelet antiaggregation agents (e.g. aspirin and dipyridamole).

In accordance with the invention, glycoprotein IIb/IIIa receptor antagonists can be administered to the patient in one oral composition such as a tablet or capsule, in several oral compositions, in one bolus injection, in a continuous intravenous administration, or any combination of oral and intravenous administration.

Suitable oral compositions include tablets, capsules (each of which includes sustained release or timed release formulations), pills, powders, granules, elixirs, tinctures, suspensions, syrups, and emulsions, or such oral compositions suitably formulated with enteric coatings. Suitable intravenous compositions include bolus or extended infusion. Such oral and intravenous compositions are well known to those of ordinary skill in the pharmaceutical arts.

The dosage regimen utilizing the active drug is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of active drug when used for the indicated effects, will range between about 0.005 mg per kg of body weight per day (mg/kg/day) to about 50 mg/kg/day and preferably 0.005–20 mg/kg/day and most preferably 0.005–10 mg/kg/day. Suitable oral tablets contain between 0.5 mg and 5 g, preferably between 0.5 mg and 2 g, most preferably between 0.5 mg and 1 g, e.g. 50 mg, 150 mg, 250 mg, or 500 mg. Oral administration may be in one or divided doses of two, three, or four times daily. The dosing objective is to achieve a level of drug for a period greater than 24 hours that is sufficient to provide at least 70% inhibition of fibrinogen binding to GP IIb/IIIa.

Intravenously, the most preferred doses will range from about 0.05 to about 50 μg/kg/minute during a constant rate infusion, to achieve a plasma level concentration during the period of time of administration of between 0.1 ng/ml and 1 μg/ml. The dosing objective is to achieve a level of drug for a period greater than 24 hours that is sufficient to provide at least 70% inhibition of fibrinogen binding to GP IIb/IIIa.

The active drug can be administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, nontoxic, pharmaceutically acceptable, inert carrier such as lactose, starch, sucrose, glucose, methyl cellulose, magnesium stearate, dicalcium phosphate, calcium sulfate, manritol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The oral compositions may also be prepared with enteric coatings to prevent release of the active drug in the stomach, providing for release of the active drug in the intestine. Such compositions are prepared with enteric coatings that are insoluble in gastric juices but readily soluble on passage into the intestine. They are prepared by mixing the active drug with an excipient, and coating the mixture with a thin polymer film.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamidephenol, polyhydroxy-ethyl-aspartamide-phenol, or polyethyleneoxidepolylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or ampehpathic block copolymers of hydrogels.

The methods are useful in percutaneous coronary angioplasty. Because of unstable plaque with thrombus, percutaneous revascularization procedures in these patients carry with them considerable higher morbidity than procedures performed in patients with stable coronary disease. Patients receive fibrinogen receptor antagonist during the procedure, and optionally, additionally, heparin and aspirin. GP IIb/IIIa receptor antagonist is continued for a period of time greater than 24 hours. Patients are evaluated at 30 days for acute coronary ischemic syndrome and the need for follow-up intervention associated with acute coronary ischemic syndrome, including coronary artery bypass grafting, repeat percutaneous intervention for acute ischemia, and insertion of a coronary endovascular stent.

Percutaneous transluminal coronary angioplasty is performed on patients having coronary blockage, e.g. stenosis. Typically, nasal oxygen and intravenous nitroglycerin are administered during the preangioplasty period and titrated to minimize the patient's pain and optimize the blood pressure. Nonionic dye is initially injected to determine whether blockage is present, and to locate blockage. Nonionic contrast dye is thereafter administered during the procedure as needed to form images of the blockage. A guide wire and catheter are inserted to guide the balloon to the blockage location. The balloon is inserted and inflated at the blockage site.

During the procedure, patients receive fibrinogen receptor antagonist and optionally aspirin and heparin. For example, patients initially receive a bolus injection of fibrinogen receptor antagonist, e.g. at a level of 10 $\mu$g/kg, prior to balloon insertion. Following the initial injection, fibrinogen receptor antagonist is administered at a rate of, for example, 0.15 $\mu$g/kg/min.

EXAMPLE 1 gp IIb/IIIa Antagonist Treatment (i.v.)

Patients with acute coronary ischernic syndrome received coronary revascularization with angioplasty. The fibrinogen receptor antagonist tirofiban (2-S-(n-Butylsulfonylamino)-3 [4-(piperidin-4-yl)butyloxyphenyl]propionic acid hydrochloride, described in U.S. Pat. No. 5,292,756) was given in a bolus injection at a dose of 10 $\mu$g/kg. Following the initial injection, tirofiban was administered at a rate of 0.15 $\mu$g/kg/min. The goal was to keep the activated clotting time between 300 and 350 seconds during the operation. Nonionic contrast dye was used to image the blockage requiring angioplasty.

Patients then received intravenous infusion of tirofiban in an amount sufficient to achieve a plasma level concentration of between 40–60 $\mu$g/ml, for 24–36 hours following angioplasty.

Patients were monitored and showed reduced acute coronary ischemic syndrome compared to patients receiving ionic contrast media.

EXAMPLE 2 gp IIb/IIIa Antagonist Treatment (i.v.)

Patients with acute coronary ischemic syndromes receive coronary revascularization with angioplasty. Aspirin is administered in a dose of 325 mg at least two hours before angiopolasty, and daily thereafter. Heparin is given intravenously in an initial bolus dose of 10,000 to 12,000 units followed by-incremental bolus doses of up to 3000 units at 15-minute intervals, but generally no more than 20,000 units is given during the procedure. Heparin is continued by constant infusion for at least 12 hours to maintain the activated partial-thromboplastin time at 1.5 to 2.5 times the. control value. The fibrinogen receptor antagonist tirofiban (2-S-(n-Butylsulfonylamino)-3[4-(piperidin-4-yl) butyloxyphenyl]propionic acid hydrochloride, described in U.S. Pat. No. 5,292,756) was given in a bolus injection at a dose of 10 $\mu$g/kg. Following the initial injection, tirofiban was administered at a rate of 0.15 $\mu$g/kg/min. Nonionic contrast dye was used to image the blockage requiring angioplasty. Aspirin is required at discharge in a dose of 325 mg per day.

Patients then received intravenous infusion of tirofiban in an amount sufficient to achieve a plasma level concentration of between 40–60 ng/ml, for 24–36 hours following angioplasty.

Patients were monitored and showed reduced acute coronary ischemic syndrome compared to patients receiving ionic contrast media.

EXAMPLE 3 gp IIb/IIIa Antagonist Treatment (i.v. and oral)

Patients with acute coronary ischemic syndrome receive coronary revascularization with angioplasty. The fibrinogen receptor antagonist tirofiban (2-S-(n-Butylsulfonylamino)-3 [4-(piperidin- 4-yl)butyloxyphenyl]propionic acid hydrochloride, described in U.S. Pat. No. 5,292,756) is given in a bolus injection at a dose of 10 μg/kg. Following the initial injection, tirofiban is administered at a rate of 0.15 μg/kg/min. The goal is to keep the activated clotting time between 300 and 350 seconds during the operation. Nonionic contrast dye is used to image the blockage requiring angioplasty.

Patients then receive intravenous infusion of tirofiban in an amount sufficient to achieve a plasma level concentration of between 40–60 ng/ml, for 24 hours following angioplasty.

Patients then receive an oral tablet containing 15 mg of the fibrinogen receptor gp IIb/IIIa antagonist 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]amino]propionic acid, described in WO 94/18981.

EXAMPLE 4

Tablet Preparation

Tablets containing 15 mg of the fibrinogen receptor gp IIb/IIIa antagonist 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid (compound 4–1) are prepared as illustrated below:

| Table for doses containing 15 mg of the gp IIb/IIIa receptor antagonist | |
|---|---|
| Ingredient | mg |
| 4-1 | 15.0 |
| Microcrystalline cellulose | 200.0 |
| Modified food corn starch | 8.5 |
| Magnesium stearate | 1.5 |

Compound 4-1, cellulose, and a portion of the corn starch are mixed and granulated to 10% corn starch paste. The resulting granulation is sieved, dried and blended with the remainder of the corn starch and the magnesium stearate. The resulting granulation is then compressed into tablets.

EXAMPLE 5

Intravenous Formulations

An intravenous dosage form of (2-S-(n-Butylsulfonylamino)-3[4-(piperidir-4-yl)butyloxyphenyl] propionic acid hydrochloride (compound 5-1) is prepared as follows:

| | |
|---|---|
| compound 5–1 | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994).

EXAMPLE 6

Intravenous Formulations

A pharmaceutical composition was prepared at room temperature using compound 5-1, a citrate buffer, and sodium chloride, to obtain a concentration of compound 5-1 of 0.25 mg/ml.

800 grams of water was introduced into a standard pharmaceutical mixing vessel. 0.25 grams of compound 5-1 was dissolved in the water. 2.7 grams sodium citrate and 0.16 grams citric acid were added to obtain a finished citrate concentration of 10 mM. 8 grams of sodium chloride was added. 200 grams of water was then added to achieve the desired final concentrations of ingredients. The resulting aqueous formulation had the following concentrations:

| Ingredient | Amount |
|---|---|
| compound 5-1 | 0.25 mg/ml |
| citrate buffer | 10 mM |
| sodium chloride | 8 mg/ml |

The finished concentrated formulation is stored in a standard USP Type I borosilicate glass container at 30–40 degrees C. Prior to compound administration, the concentrated formulation is diluted in a 4:1 ratio resulting in a finished concentration of 0.05 mg/ml and transferred to an infusion bag.

The following table shows the percentage of ischemic events, including death, nonfatal myocardial infarction, revascularization, and insertion of a coronary endovascular stent, 2 days following PTCA. 764 patients received ionic contrast media during the PTCA prodedure, while 1355 patients received nonionic contrast media. Patients in each group also received either placebo or tirofiban.

TABLE 1

| Incidence of ischemic events 2 days following PTCA | |
|---|---|
| PTCA Treatment | % |
| Nonionic contrast media/tirofiban | 4.9 |
| Ionic contrast media/tirofiban | 6.3 |
| Ionic contrast media/placebo | 7.6 |
| Nonionic contrast media/placebo | 9.5 |

Incidence of ischemic events is represented as a percentage of total patients studied. Lower percentages are associated with a lower number of ischemic events.

The data clearly show a dramatic benefit to using nonionic contrast media for PTCA when glycoprotein IIb/IIIa receptor antagonists are administered. Whereas ionic contrast media, when no glycoprotein IIb/IIIa receptor antagonist is employed, corresponds with lower incidence of ischemic events (as compared with incidence of ischemic events with nonionic contrast media and no glycoprotein IIb/IIIa receptor antagonist), nonionic contrast media is preferred over ionic contrast media for PTCA procedures involving glycoprotein IIb/IIIa receptor antagonist administration.

What is claimed is:

1. A method for treating a patient having coronary artery blockage which comprises
   a) introducing nonionic contrast dye into the coronary artery having blockage to image the blockage,
   b) administering a fibrinogen receptor antagonist to the patient, and inserting a balloon catheter into the blockage and inflating the balloon at the location of the blockage to revascularize the artery, and
   c) administering fibrinogen receptor antagonist to the patient following balloon inflation wherein the fibrinogen receptor antagonist is administered in a therapeutically effective amount sufficient to provide at least 70% inhibition of fibrinogen binding to GP IIb/IIIa.

2. A method of claim 1 wherein the fibrinogen receptor antagonist is administered to the patient according to step c) for a period of time of at least 24 hours.

3. A method of claim 1 wherein the fibrinogen receptor antagonist is orally administered.

4. A method of claim 3, wherein the fibrinogen receptor antagonist is selected from the group consisting of 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid, Methyl-$N^3$-[2-{3-(4-formamidinophenyl)-isoxazolin-5(R)-yl}-acetyl]-$N^2$-(n-butyloxycarbonyl)-2,3-(S)-diaminopropionate acetate salt, Ethyl 3-[[4-[[4-(aminoiminomethyl)phenyl]amino]-1,4-dioxobutyl]amino]-4-pentynoate, and, (R)-methyl-3-[[[3-[4-(aminoiminomethyl)phenyl]-4,5-dihydro-5-isoxazolyl]acetyl]amino]-N-(butoxycarbonyl)-L-alanine monoacetate.

5. A method of claim 1 wherein the fibrinogen receptor antagonist is intravenously administered.

6. A method of claim 5, wherein the fibrinogen receptor antagonist is selected from the group consisting of Mpr-(Acetimidyl-Lys)-Gly-Asp-Trp-Phe-Cys-$NH_2$, Mpr-(Acetimidyl-Lys)-Gly-Asp-Trp-Phe-Pen-$NH_2$, Mpr-(Phenylimidyl-Lys)-Gly-Asp-Trp-Phe-Pen-$NH_2$, Mpr-(Phenylimidyl-Lys)-Gly-Asp-Trp-Phe-Cys-$NH_2$, N-Methyl-D-phenylalanyl-N-[(1S)-1-formyl-4-guanidinobutyl]-L-prolinamide, ((1-(2-((4-(aminoiminomethyl)benzoyl)amino)-3-(4-hydroxyphenyl)-1-oxopropyl)-4-piperidinyl)oxy)-(S)-acetic acid, N-(2-(2-(((3-((aminoiminomethyl)amino)propyl)amino)carbonyl)-1-piperidnyl)-1-(cyclohexylmethyl)-2-oxoethyl)-(R,S)-glycine, and (2-S-(n-Butylsulfonylamino)-3[4-(piperidin-4-yl)butyloxyphenyl]propionic acid hydrochloride.

7. A method of claim 5 wherein the fibrinogen receptor antagonist is Mpr-(Har)-G-D-W-P-C-$NH_2$.

* * * * *